United States Patent [19]
Eaton

[11] Patent Number: 5,700,288
[45] Date of Patent: Dec. 23, 1997

[54] BREAST PROSTHESIS

[75] Inventor: L. Daniel Eaton, Little Rock, Ark.

[73] Assignee: The Board of Trustees of the University of Arkansas, Little Rock, Ark.

[21] Appl. No.: 683,816

[22] Filed: Jul. 18, 1996

[51] Int. Cl.$^6$ .................. A61F 2/52; A41C 3/10
[52] U.S. Cl. ........................... 623/7; 450/55
[58] Field of Search ............ 623/7, 8; 450/54, 450/55

[56] References Cited

U.S. PATENT DOCUMENTS

| | | | |
|---|---|---|---|
| 3,255,754 | 6/1966 | Brumberger | 450/55 |
| 3,641,592 | 2/1972 | Den Bleyker | 623/7 |
| 3,845,507 | 11/1974 | Kirby et al. | 3/36 |
| 4,024,876 | 5/1977 | Penrock | 128/472 |
| 4,245,644 | 1/1981 | Evans | 128/476 |
| 4,364,880 | 12/1982 | Howse | 264/28 |
| 4,369,792 | 1/1983 | Miller | 128/479 |
| 4,401,492 | 8/1983 | Pfrommer | 156/61 |
| 4,600,551 | 7/1986 | Erb | 264/222 |
| 4,637,398 | 1/1987 | Sherwood | 128/478 |
| 4,681,587 | 7/1987 | Eberl et al. | 623/7 |
| 4,699,144 | 10/1987 | Sherwood | 450/54 |
| 4,826,501 | 5/1989 | Grundei | 623/8 |
| 5,019,101 | 5/1991 | Purkait et al. | 623/8 |
| 5,035,758 | 7/1991 | Degler et al. | 156/61 |
| 5,066,302 | 11/1991 | Rice | 623/7 |
| 5,071,433 | 12/1991 | Naestoft et al. | 623/7 |
| 5,098,330 | 3/1992 | Greenberg | 450/55 |
| 5,116,370 | 5/1992 | Foglietti | 623/8 |
| 5,215,494 | 6/1993 | Flanagan | 450/61 |
| 5,352,307 | 10/1994 | Wild | 156/66 |
| 5,354,337 | 10/1994 | Hoy | 623/7 |
| 5,376,323 | 12/1994 | Eaton | 264/222 |

FOREIGN PATENT DOCUMENTS 4115428  11/1992  Germany ..................... 623/7

Primary Examiner—Mary Beth Jones
Attorney, Agent, or Firm—Ray F. Cox, Jr.

[57] ABSTRACT

A breast prosthesis and an underwire bra adapted to retain the breast prosthesis. The breast prosthesis is affixed to the underwire bra by an attachment fixture molded into the posterior (or chest side) of the prosthesis. The attachment fixture, a female plug, is complementary to a retention fixture, a male plug, molded into a loop on the underwire of the bra. The loop of the underwire is adapted to provide a spring bias of the male plug against the chest wall of the wearer for a secure and comfortable fit and to provide sensory feedback as to the correct positioning of the prosthesis.

12 Claims, 6 Drawing Sheets

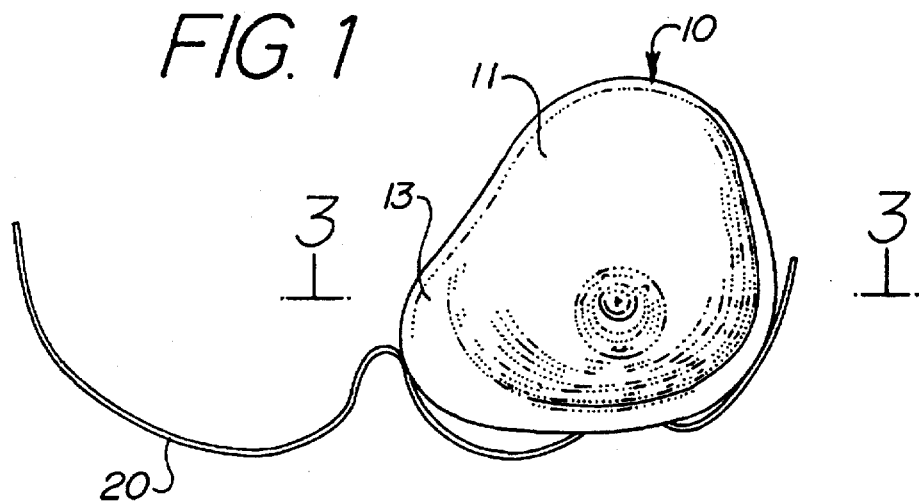
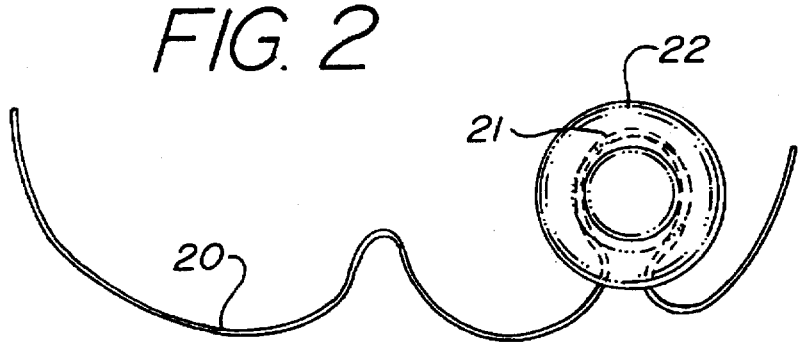
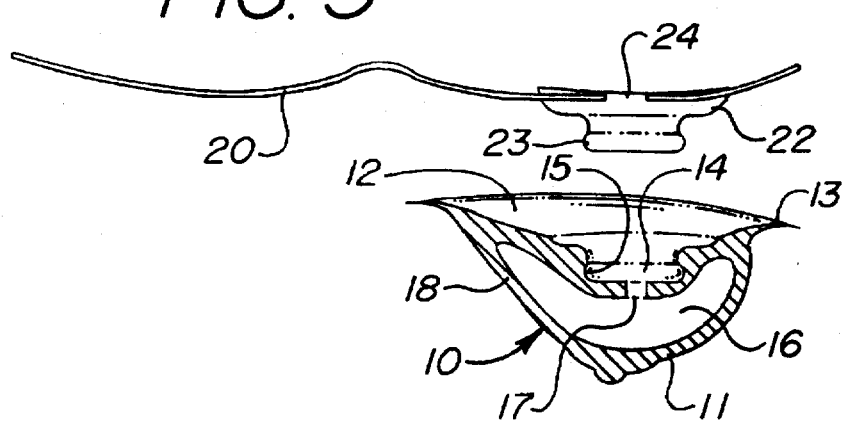

BREAST PROSTHESIS

BACKGROUND OF THE INVENTION

The present invention relates to a breast prosthesis to be worn in conjunction with an underwire bra adapted to be attached to the breast prosthesis, and to a method of making a breast prosthesis designed to be attached to an underwire bra.

Breast prostheses are necessary for women who have undergone radical mastectomies. An acceptable breast prosthesis should replicate the appearance of the natural breast while being comfortable to wear. The prior art of breast prostheses shows a number of attempts to achieve one or the other of these objectives, although with limited success at achieving both. Among the problems not completely solved in the prior art include achieving a natural look and feel to the prosthesis. Related to this problem is the perceived need to maintain a balanced weight of the prosthesis vis-a-vis the remaining natural breast. This may in fact be less of a problem with actual wearers who are likely to feel that weight is less of a concern than maintaining a natural relationship between the prosthesis and the chest of the wearer. Many patients complain that the location of the prosthesis in relation to the chest wall shifts and there is nothing in the way of "feedback" to the wearer that the prosthesis is in the correct position. An additional problem not well addressed by the prior art is the method of attachment or wearing of the breast prosthesis by the patient. One common solution is to attach the prosthesis directly to the chest of the patient with adhesives. This is obviously an uncomfortable solution and not always effective. Furthermore, a tight adhesive fit to the chest traps heat and prevents ventilation of the skin surface. Another common answer is to place the prosthesis in a pocket of a bra. This is also not a complete answer as the prosthesis may shift out of position within the bra, and, even if securely placed in the bra, does not have a natural feel to the wearer since it does not maintain its position with respect to the chest as is true of a natural breast.

It is known to use male and female connector snaps in conjunction with a breast prosthesis. U.S. Pat. No. 5,116,370 issued to Foglietti on May 26, 1992 for "Breast Prosthesis with Female and Male Adapter Snaps" discloses implantable breast prostheses which allows the stacking of implants "without fear of slippage and subsequent cosmetic deformity." While used in conjunction with breast prostheses, the Foglietti device is not used in conjunction with an external breast prosthesis nor in conjunction with a fixture for retaining the external breast prosthesis in a natural position through the use of a modified underwire bra.

It is also known to employ a spring-like underwire system in conjunction with a bra. U.S. Pat. No. 4,245,644 issued to Evans on Jan. 20, 1981 for "Breast Prosthesis or Augmenting Form Including Spring-Mass System" discloses a cantilevered spring support system for use in conjunction with a breast prosthesis or in a conventional bra to enhance natural breast movement. A weight is provided on the cantilevered spring for enhancing the movement effects of natural or prosthetic breasts. While Evans discloses a spring-like underwire system used in conjunction with a bra and breast prosthesis, the spring of Evans does not perform any function related to retaining a breast prosthesis or to providing a natural feel to the wearer of the breast prosthesis. In particular, Evans does not disclose a plug formed into the underwire spring for attachment to the breast prosthesis, nor the use of a spring to provide sensory feedback to the wearer concerning the location of the breast prosthesis in relation to the chest wall.

There are a number of patents related to the use of adhesive or hook and loop fasteners for affixing a breast prosthesis to the skin of the wearer or to a bra, such as U.S. Pat. No. 5,071,433. This and similar patents are not considered relevant to the present invention other than to describe the general state of the art in breast prosthesis fixation means.

There are also a number of patents related to breast prostheses in general; for example, U.S. Pat. Nos. 3,845,507; 4,826,501; and 5,066,302; in methods of forming breast prostheses; for example, U.S. Pat. Nos. 4,364,880; 4,600,551; 4,401,492; 5,035,758; and 5,352,307; and in bras for use in conjunction with breast prostheses; for example, U.S. Pat. Nos. 4,024,876; 4,369,792; 4,637,398; and 4,699,144. These patents are likewise considered relevant to the general state of the art but not particularly to the present invention.

The prior art does not show a breast prosthesis formed with a posterior female plug connector. Nor does the prior art show a male plug connector formed into an underwire bra for use in conjunction with a breast prosthesis. Further, the prior art does not show a male plug connector formed into a loop of underwire assembled into a bra for use in conjunction with a breast prosthesis. Finally, the prior art does not show a plug connector for a breast prosthesis in conjunction with a loop of underwire to act as a spring to assist in the natural retention of the breast prosthesis against the skin of the chest wall of the patient and to provide natural sensory feedback of the proper location of the breast prosthesis in relation to the chest wall.

These and other problems and disadvantages of the prior art are overcome by the present invention as described below.

SUMMARY OF THE INVENTION

The present invention comprises two main components: a breast prosthesis and an underwire bra adapted to retain the breast prosthesis. The breast prosthesis is preferably made using the technique disclosed in U.S. Pat. No. 5,376,323, the disclosure of which is incorporated herein by reference, by the inventor of the present invention as described more fully below. The breast prosthesis is advantageously formed to match the remaining natural breast in shape, skin tint, etc. The breast prosthesis is hollow with the thickness of the walls varied as necessary to provide an acceptable firmness and resilience. The thickness of the walls may vary from one part of the prothesis to another as necessary to impart the desired mechanical properties. In addition, the breast prothesis may be filled with materials to alter the weight, resilience and other characteristics of the prothesis. For example, a saline solution may be injected into the hollow of the prosthesis in order to adjust the weight of the prosthesis to match the weight of the remaining natural breast or to match the perceived weight of the natural breast or to adjust the weight of the prosthesis for a comfortable sensation to the wearer without regard to the actual weight of the natural breast. A foam material may be added to the hollow of the breast prothesis in order to adjust both the weight and resilience of the prosthesis. The firmness and resilience of the prosthesis may also be adjusted by the addition of an amount of air at slightly greater than atmospheric pressure. The addition of any material, including air, saline solution or other substance, may be effected though a self-sealing valve imbedded in the prosthesis. Such self-sealing valves are well known in the art; for example, see the self-sealing valve disclosed in U.S. Pat. No. 5,019,101, the disclosure of which is incorporated herein by reference. It is desirable to place the valve in an inconspicuous location on the breast prosthesis. In the preferred embodiment of the present invention the valve is located on the back side of the prosthesis within an attachment fixture to be described more fully below. The valve may be embedded in the material of the breast prosthesis and covered with room temperature vulcanizable silicone (RTV), such as Silastic (Reg. trademark of Dow Corning) or similar material to completely seal it within the material of the breast prosthesis.

The breast prosthesis may be custom made for a particular patient or may be of a standard type. In the latter case, a range of sizes and shapes may be employed to assure a compatible version for each individual patient. Using the technique of U.S. Pat. No. 5,376,323, the breast prosthesis is formed as follows: A two-part mold is prepared to form the breast prosthesis. The mold is injected with RTV silicone. The mold and RTV silicone is maintained at a fixed temperature for a known period of time to allow a vulcanized layer of RTV silicone to form adjacent to the surfaces of the mold. The prosthesis is then removed from the mold and the remaining unvulcanized RTV silicone expressed from the interior of the prosthesis to form a hollow.

A mold is taken of the patient's torso to ensure the proper shape for the posterior side of the breast prosthesis. The anterior of the breast prosthesis may be a mirror image of the patient's remaining natural breast produced by techniques well known in the art or a standard mold may be used to produce the shape of the anterior of the prosthetic breast. The shape of the chest side of the breast prosthesis is preferably convex as is known in the art to avoid direct contact with the skin which inhibits proper ventilation of the skin surface. Only the periphery of the breast prosthesis actually touches the skin of the wearer. The periphery is "feathered-out" so as to blend in with the skin of the wearer. By careful attention to skin coloring and other factors, the breast prosthesis may be manufactured to give a naturalistic appearance. It should be understood that the present invention is not limited to breast prostheses made in this manner however. Breast prostheses manufactured by other techniques may be readily employed in the practice of the present invention.

The breast prosthesis is affixed to the underwire bra by an attachment fixture molded into the posterior (or chest side) of the prosthesis. The attachment fixture, a female plug, is complementary to a retention fixture, a male plug, on the underwire bra. An example of an underwire bra is disclosed in U.S. Pat. No. 5,215,494, the disclosure of which in incorporated herein by reference. In the preferred embodiment, the attachment fixture is formed into the posterior of the prosthesis as an indentation with a ridge around the rim of the indentation. (The self-sealing valve mentioned above is located at the bottom of the indentation.) Since the prosthesis is formed from a flexible plastic material, it may readily be seen that the attachment fixture is elastic enough to accept and hold a complementary shape in the nature of a plug. A retention fixture formed in a shape complementary to the attachment fixture is affixed to the underwire bra in a manner described below. The retention fixture is also formed of a flexible elastic material, such as RTV silicone so that the retention fixture, when inserted into the attachment fixture, is removably locked into position and thereby the breast prosthesis is removably locked to the underwire bra. In use the wearer simply dons the underwire bra in a normal fashion. The cup, which is adapted to receive the breast prosthesis is lowered, thereby exposing the retention fixture on the underwire bra. The breast prosthesis is fixed into position by "plugging" the retention fixture into the attachment fixture. The cup of the bra may then be positioned to cover the breast prosthesis and the strap assumed over the shoulder. Removing the breast prosthesis is simply the reverse of the steps described above.

The underwire bra is adapted to receiving and retaining the breast prosthesis as described following. A typical underwire bra uses a wire as structural element of the bra. The underwire typically runs under the lower edge of the bra where it is affixed to the material of the bra. The underwire is shaped to the torso of the wearer and provides support and shaping to the breasts. In the preferred embodiment of the present invention, the underwire is shaped normally under the natural breast. However, for the prosthesis, the underwire is formed with a loop to hold the retention fixture. The center of the loop is placed so as to center the breast prosthesis in a natural position. Furthermore, the underwire loop is shaped so as to gently press against the chest of the wearer so as to provide tactile feedback regarding the presence of the prosthesis in the correct position on the chest wall. This gentle pressure also ensures that the prosthesis is less likely to slip out of the correct position, further contributing to the sense of security of the wearer.

The underwire and retention fixture are formed in the following manner. A two piece mold is used to form the retention fixture. The lower mold forms the shape complementary to the attachment fixture. The upper mold may be formed from a cast taken of the torso of the wearer so that the portion of the retention fixture formed by the upper mold fits exactly against the contours of the portion of the chest of the user where the prosthesis is intended to be located. The underwire is formed with a loop at the point where the retention fixture is to be located. The underwire loop is placed into the lower mold where it is held in position by a pair of grooves cut into the side of the mold. The upper mold is placed into position on the lower mold. A quantity of RTV silicone is injected into the mold and maintained for a period of time to allow the silicone to harden. It should be understood that the underwire loop is completely embedded in the hardened silicone so that no part of the underwire loop contacts the chest of the wearer. A certain amount of shaping of the underwire by eye is possible while the underwire is in the mold. For example, the wire may be shaped to provided the spring action described above to hold the retention fixture against the chest of the wearer.

After the silicone has hardened, the mold is opened and the retention fixture and underwire are removed. The retention fixture may be annealed to improve its toughness. The final shaping of the underwire is done by hand on a torso cast of the chest of the wearer to ensure that the shape of the underwire is correctly adapted to the contours of the wearer's torso and to provide the requisite degree of "springiness" of the underwire loop embedded in the retention fixture. To ensure that the underwire loop is shaped to provide the correct amount of pressure against the chest of the wearer, the torso cast may be modified from the actual shape of the patient's chest to provide for a slight depression in the cast at the correct position. When the underwire loop is shaped to the depression, it must necessarily provide a degree of pressure when the underwire bra and prosthesis are worn by the patient. The underwire with the molded-in retention fixture is then incorporated into the bra in the conventional fashion with the exception that the underwire loop and retention fixture are not enclosed within the material of the bra as is the case with the remaining conventional portion of the underwire. The back of the retention fixture, however, may be provided with a cotton pad or the like to improve comfort and to allow the skin of the wearer to breathe. The final shaping of the underwire may conveniently be done on the patient to ensure the proper fit and comfort.

It is therefore an object of the present invention to provide for a breast prosthesis to be worn in conjunction with an underwire bra modified to incorporate a retention fixture.

It is a further object of the present invention to provide for a breast prosthesis and retention means which provides for natural placement and retention of the breast prosthesis on the chest of the wearer.

It is an additional object of the present invention to provide for a breast prosthesis and retention means which provides natural sensory feedback to the wearer so as to provide a comfortable and secure sensation to the wearer.

These and other objects and advantages of the present invention will be apparent from a consideration of the following detailed description of the preferred embodiments in conjunction with the drawings which are briefly described as follows:

BRIEF DESCRIPTION OF THE DRAWINGS

FIG. 1 is a front elevation view of the breast prosthesis and underwire retention fixture of the present invention.

FIG. 2 is a front elevation view of the underwire retention fixture.

FIG. 3 is a top plan view of the breast prosthesis in section and the underwire retention fixture.

DETAILED DESCRIPTION OF THE PREFERRED EMBODIMENTS

Figure 4:
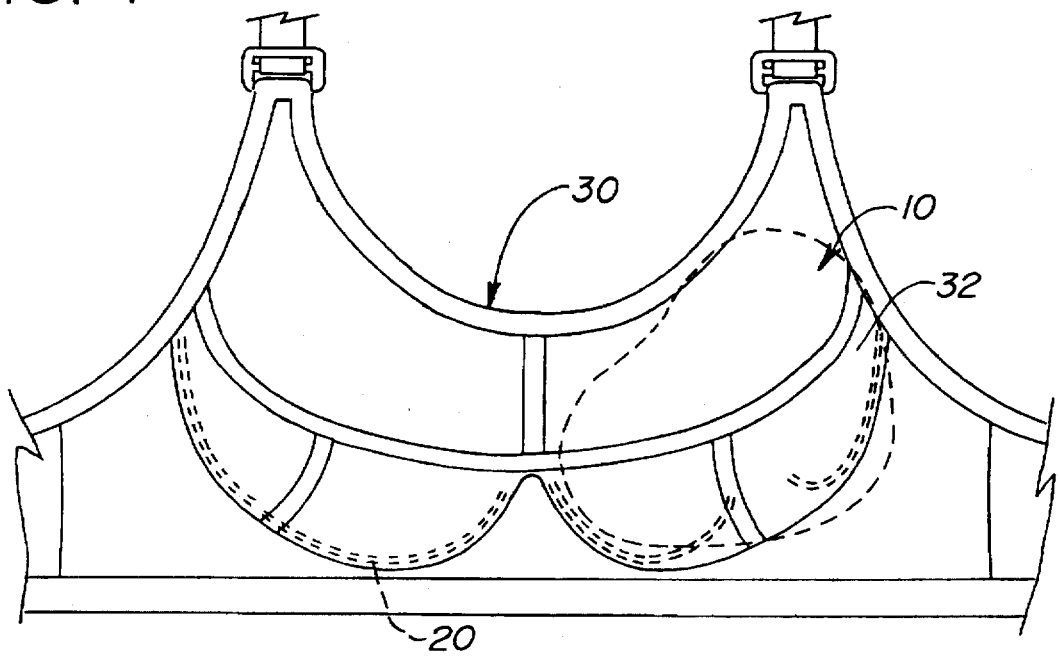
FIG. 4 is a front elevation of an underwire bra as modified for the practice of the present invention with the underwire and breast prosthesis shown in outline.

The preferred embodiments of the present invention may be described with reference to FIGS. 1, 2 and 3. The present invention comprises two main components: a breast prosthesis and an underwire bra adapted to retain the breast prosthesis. The breast prosthesis 10 may be constructed by any of various techniques known in the art, including the method described more fully below. In typical underwire bras, the underwire is shaped to conform to the chest wall of the wearer and to shape and support the breasts. In the present invention, the underwire 20 is modified to form a loop 21 centered on the mastectomy site. A male plug 22 is molded onto the loop 21 in a manner to be described below.

The breast prosthesis anterior 11 is molded into a shape which mimics the appearance of a natural breast, while the breast prosthesis posterior 12 is essentially convex in shape with feathered-out edges 13 to conform and blend with the chest wall of the wearer. The convex shape of the breast prosthesis posterior 12 minimizes contact with the skin of the wearer so as to prevent discomfort from the trapping of warmth and moisture. The breast prosthesis posterior 12 is further provided with a female plug 14 which is complementary to the shape of the male plug 22. While various forms of snapwise attachments may be employed to form the male plug 22 and the female plug 14, the preferred embodiment employs a male plug 22 with a circular rim 23 which is snapwise received into a matching groove 15 in the female plug 14. As will be described more fully hereinafter, the preferred construction of the breast prosthesis 10 and the male plug 22 employs elastic materials so that the male plug 22 may be snapwise received into the female plug 14 to form a releasable interconnection between the two.

Using the method described below to form the breast prosthesis 10 results in a breast prosthesis 10 with a hollow interior 16. The hollow interior 16 may be left hollow, may be filled with air or other gaseous material at slightly greater than atmospheric pressure, may be filled partially or wholly with liquid such as saline solution, or may be filled partially or wholly with foam material. These various types of filling materials serve to provide flexibility in adjusting the weight and resilience of the breast prosthesis to ensure a comfortable feel to the wearer as well as an appearance that closely mimics the natural breast. These various fill materials may be introduced through a self-sealing valve 17. In the preferred embodiment, the self-sealing valve 17 is advantageously placed at the bottom of the indentation formed by the female plug 14.

In preparing a breast prosthesis 10 for use in the practice of the present invention, it may be desirable to adjust the thickness of the wall 18 of the breast prosthesis 10 so as to produce a natural shape and resilience to the breast prosthesis 10.

As noted above, the underwire 20 is shaped to conform to the chest wall of the wearer. It is a significant feature of the present invention that the loop 21 formed in the underwire 20 is also shaped so as to bias the posterior side 24 of the male plug 22 against the chest wall of the wearer. Since the underwire 20 is typically constructed from a springy metal, this is accomplished by bending the loop 21 toward the chest wall of the wearer. This may be accomplished, for example, by taking a torso cast of the wearer and then modifying the torso cast by forming a slight depression at the preferred location for the male plug 22. The loop 21 and underwire 20 are then shaped so as to conform to this modified torso cast. Additionally, the underwire 20 and loop 21 may be custom shaped by hand to provide the most desirable fit for a particular wearer. While it may be desirable that the posterior side 24 of the male plug 22 conform to the shape of the chest wall of the wearer at the preferred point of contact, such intimate contact may be undesirable in that warmth and moisture may be trapped between the male plug 22 and the skin of the wearer. To avoid this situation, a pad of cotton or other suitably porous material may be employed on the posterior side 24 of the male plug 22 so as to provide cushioning and ventilation.

Figure 5:
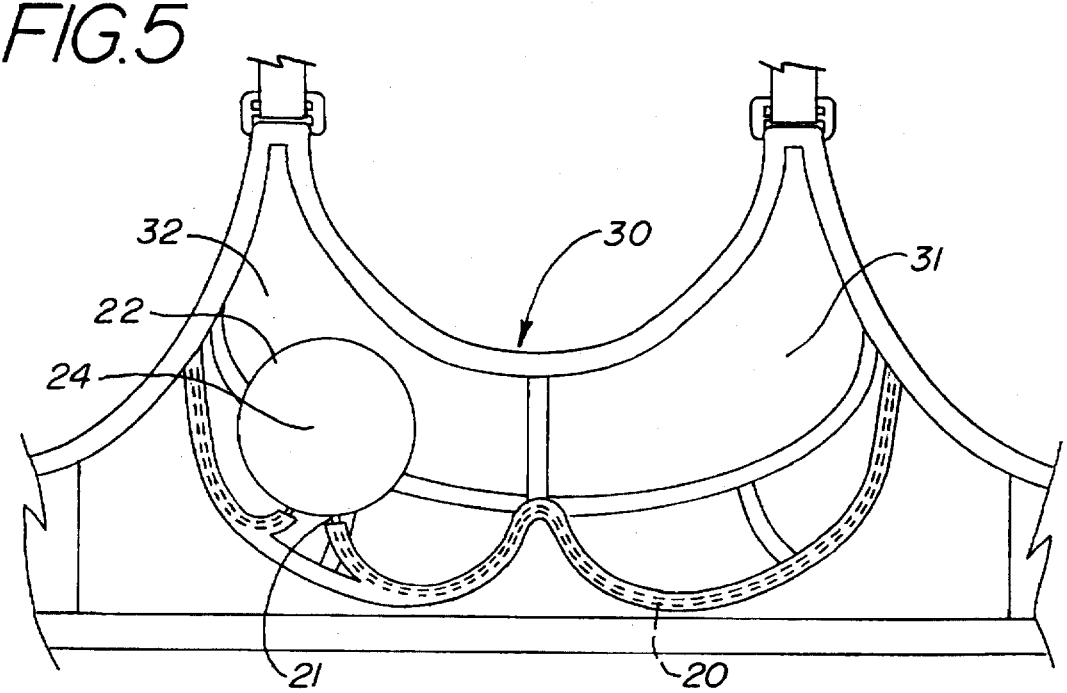
FIG. 5 is a rear elevation of an underwire bra as modified for the practice of the present invention. The breast prosthesis is not shown.
Figure 6:
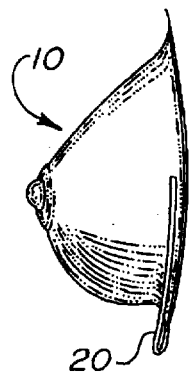
FIG. 6 is a left side elevation of the breast prosthesis and underwire retention fixture. The underwire bra is not shown for clarity.
Figure 7:
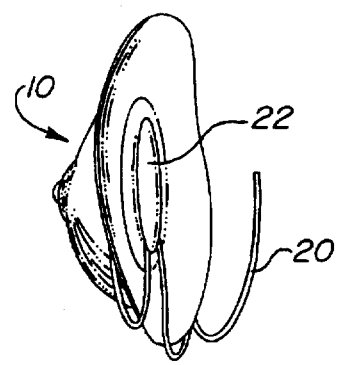
FIG. 7 is a left-rear oblique elevation view of the breast prosthesis and underwire retention fixture of FIG. 6.
Figure 8:
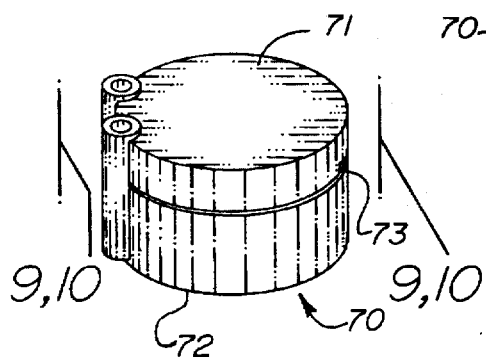
FIG. 8 is a perspective view of a two-part mold suitable for the method of forming the male plug of the underwire retention fixture.

A typical underwire bra is shown in FIGS. 4 and 5. The underwire 20 is fastened to the bra 30 using conventional techniques. As shown in FIGS. 4 and 5, a cup 31 for a natural breast is conventional in configuration and essentially indistinguishable from a conventional underwire bra. The cup 32 for receiving the breast prosthesis 10 is altered from the appearance of a conventional underwire bra in that the male plug 22 is positioned toward the center of the cup 32 in the appropriate position to be attached to the breast prosthesis 10 and to provide the appropriate degree of sensory feedback to the chest wall of the wearer. Except for a small portion of the loop 21, the underwire 20 is otherwise unobservable.

Figure 13:
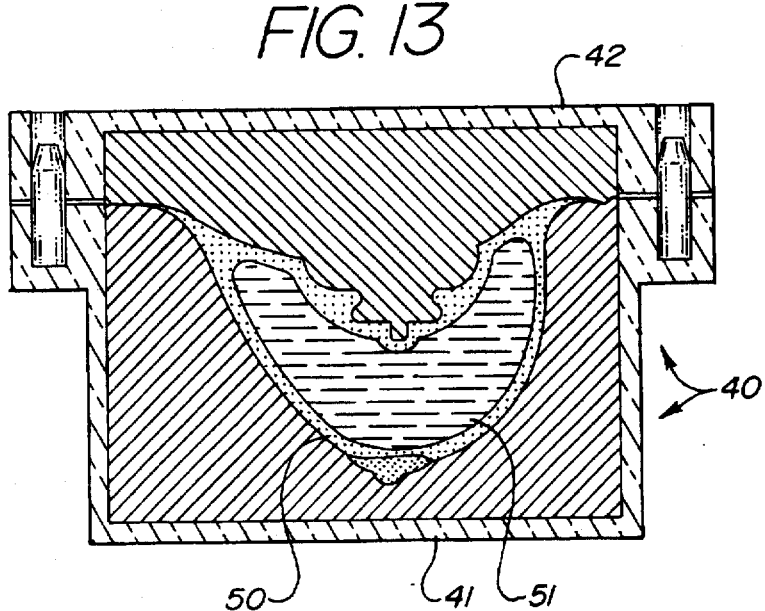
FIG. 13 is a sectional elevation view of the two-part mold of FIG. 12 after injection of the mold with RTV silicone and after a layer of vulcanized RTV silicone has formed adjacent to the walls of the mold.
Figure 14:
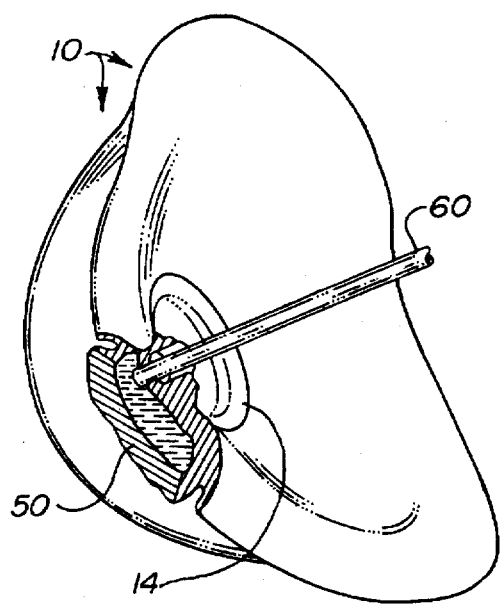
FIG. 14 is a perspective view of the posterior of the breast prosthesis removed from the mold. In section, a hollow instrument inserted into the indentation of the attachment fixture on the posterior of the breast prosthesis is shown penetrating the vulcanized layer of RTV silicone into the unvulcanized interior.

The construction of the breast prosthesis 10 may be described with reference to FIGS. 6, 7 and 11 through 18. A two part mold 40 is prepared in which the lower half 41 provides the appropriate shape for the anterior 11 of the breast prosthesis 10 and the upper half 42 provides the appropriate shape for the posterior 12 of the breast prosthesis 10. The anterior 11 may be derived from a standard array of breast shapes or may be custom designed to a particular patient. The posterior 12 is convex in general shape with the standard female plug shape disposed therein. The outer feathered edges are desirably shaped to the chest structure of the individual patient for a comfortable and unobtrusive fit. As shown in FIG. 13, the interior of the mold 40 is injected with a quantity of RTV silicone. The Silastic brand of RTV silicone manufactured by Dow Corning has been found to be suitable to the formation of a hollow prosthesis according to the method described below, which is the subject of U.S. Pat. No. 5,376,323. After the injection of the RTV silicone, a suitable amount of time is allowed for the RTV silicone to form a wall 50 adjacent to the surface of the upper mold 42 and lower mold 41. Unvulcanized RTV silicone 51 remains in the interior. The amount of time required to achieve a particular wall thickness is known in the prior art as set forth in FIG. 18.

Figure 15:
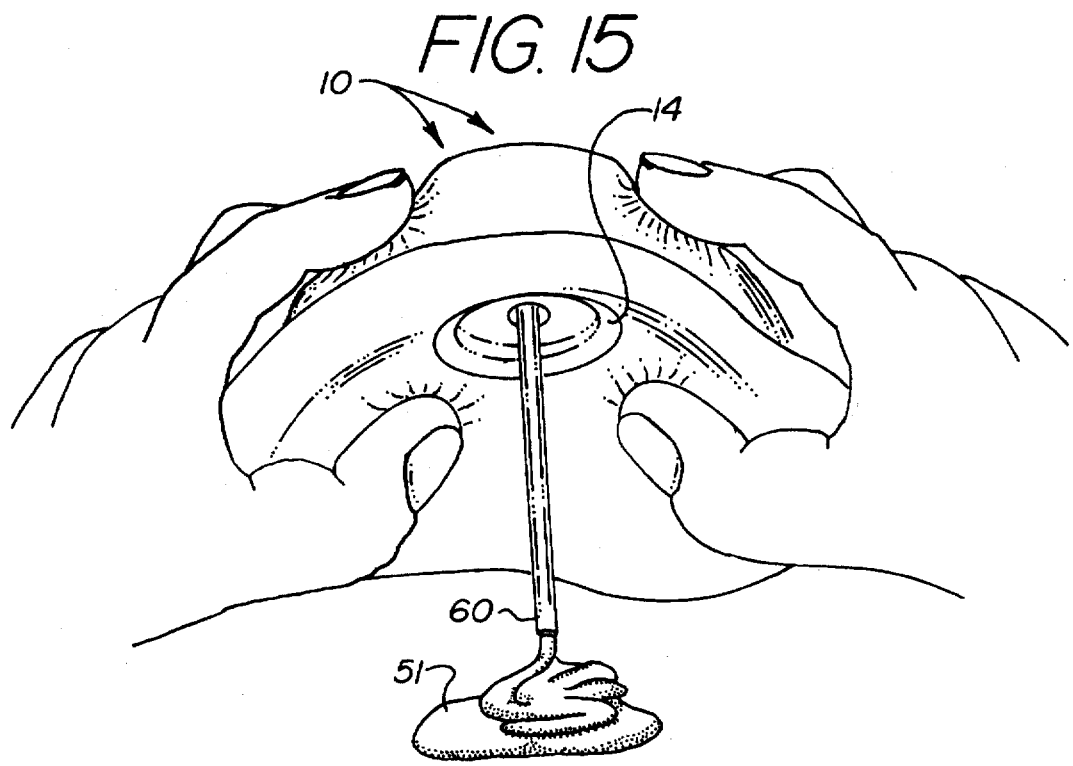
FIG. 15 is a perspective view of the posterior of the breast prosthesis showing the unvulcanized RTV silicone expressed from the interior.
Figure 18:
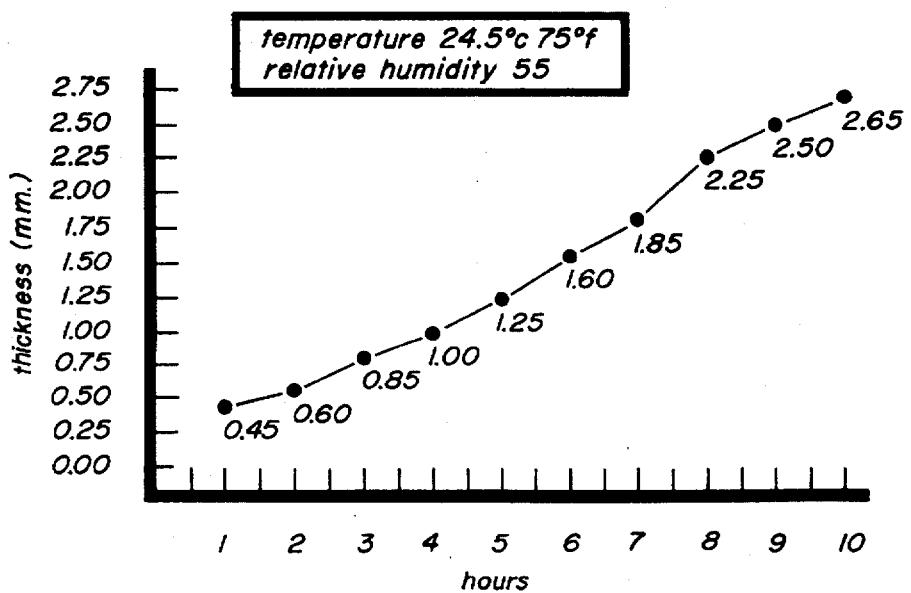
FIG. 18 is a diagram of the prior art showing the relationship between the time after injection of RTV silicone into a mold and the resultant wall thickness.

The breast prosthesis 10 may then be removed from the mold 40 and an appropriate hollow instrument 60 inserted through the wall 50 of the breast prosthesis 10 to gain access to the unvulcanized RTV silicone 51 in the interior of the breast prosthesis 10. As shown in FIG. 15, the unvulcanized RTV silicone 51 may then be expressed from the interior of the breast prosthesis 10.

Figure 16:
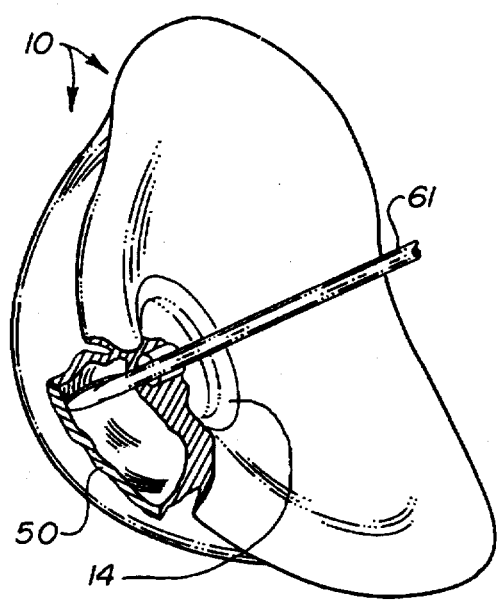
FIG. 16 is a perspective view of the posterior of the breast prosthesis showing in section the use of an instrument to shape the interior of the breast prosthesis to produce the desired wall thickness in particular locations.

As shown in FIG. 16, a spatula 61 or similar instrument may be introduced into the interior of the breast prosthesis 10 so as to assist in removing unvulcanized RTV silicone, to place unvulcanized RTV silicone in suitable areas to adjust the wall thickness of the breast prosthesis 10 and to close the opening made through the wall 50 of the breast prosthesis 10. It may also be desirable to insert a self-sealing valve 17 into the area of the female plug 14 at this point. The self-sealing valve 17 may also be formed into the breast prosthesis 10 by placing the self-sealing valve 17 into the mold prior to introducing the RTV silicone into the mold.

Figure 17:
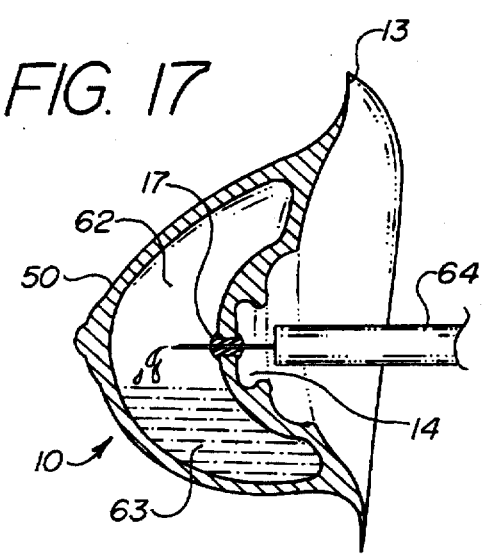
FIG. 17 is a sectional elevation view of the breast prosthesis showing the injection of material, such as saline, into the interior of the prosthesis.
Figure 10:
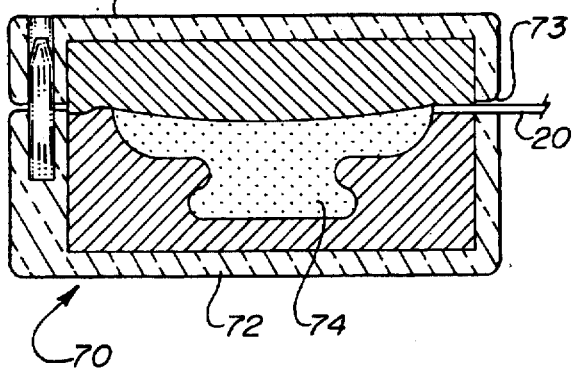
FIG. 10 is a sectional elevation view of the two-part mold showing the mold injected with RTV silicone.
Figure 11:
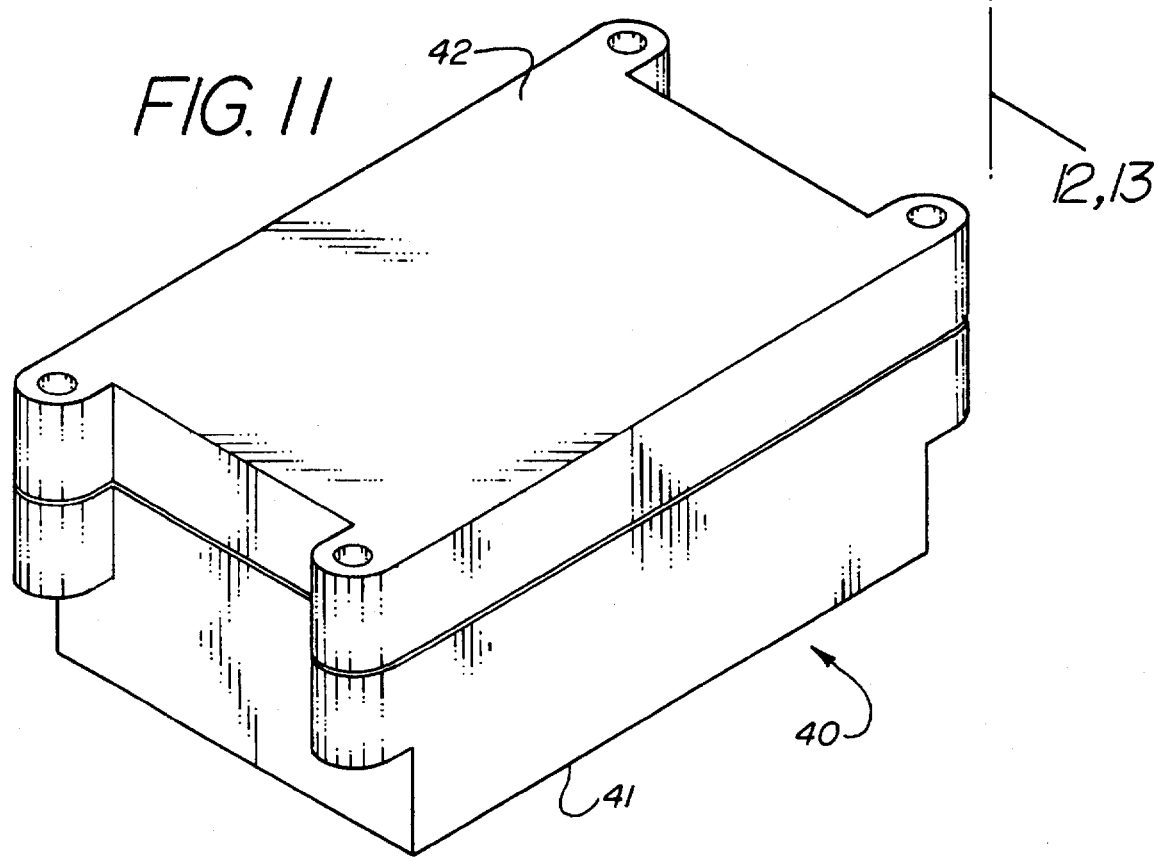
FIG. 11 is a perspective view of a two-part mold for forming the breast prosthesis.
Figure 12:
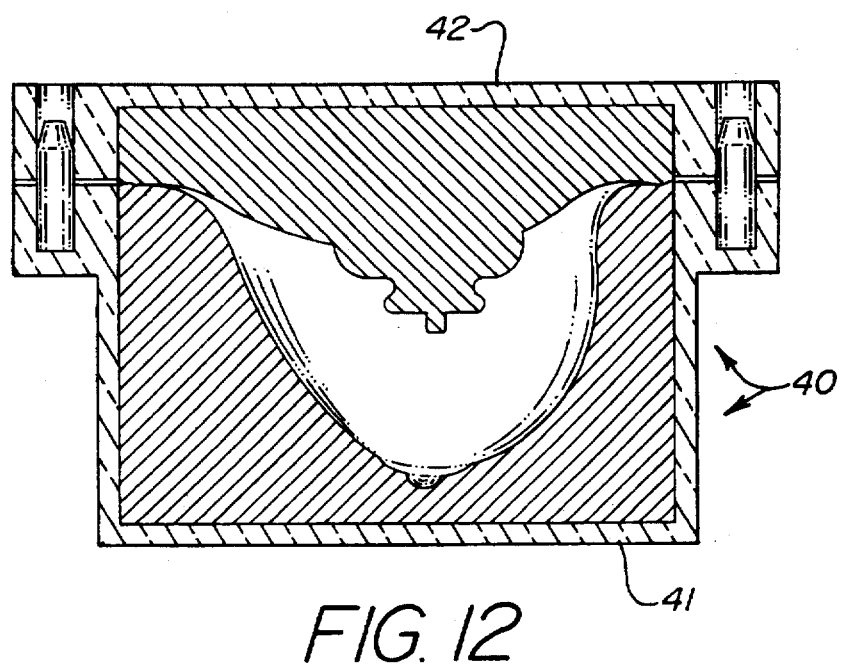
FIG. 12 is a sectional elevation view of the two-part mold of FIG. 11 showing the shapes of the upper and lower molds for forming the breast prosthesis.

A self-sealing valve 17 is shown so positioned in FIG. 17. Once the breast prosthesis 10 has completely cured, filling materials may be introduced into the interior 62 of the breast prosthesis 10. FIG. 17 illustrates a particular process by which saline solution 63 may be injected by hypodermic 64 through the self-sealing valve 17 into the interior 62 of the breast prosthesis 10. As described previously, various types of filling materials may be employed to provide a natural weight or feel to the breast prosthesis 10.

Figure 9:
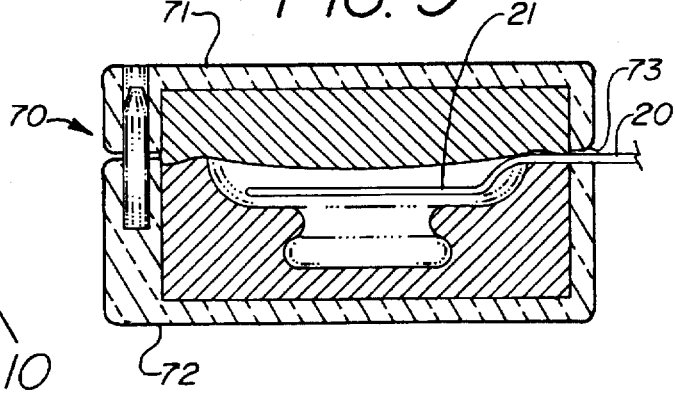
FIG. 9 is a sectional elevation view of the two-part mold showing shape of the upper and lower molds for forming the male plug. The underwire loop is shown placed in the mold prior to the injection of RTV silicone.

The construction of the male plug 22 may be described with reference to FIGS. 6 through 10. A two part mold 70 is prepared in which the upper half 71 provides the appropriate shape for the posterior side 24 of the male plug 22 so as to conform to the chest wall of the user at the desired location and the lower half 72 provides the appropriate complementary shape for releasably interconnecting with the female plug 14. Once the two portions of the mold 70 are prepared as shown in FIG. 9, the underwire 20 is placed in the mold 70 so that the underwire loop 21 is positioned inside the mold 70. Grooves 72 may be made in the edges of the upper half 71 or lower half 72 of the mold 70 so as to receive and position the underwire 20 properly. After positioning the underwire 20 in the mold, the underwire 20 may be shaped by hand to the approximate curvature of the chest wall of the patient and may also receive some shaping to assist in providing the requisite spring bias against the chest wall of the patient. The mold 70 is then filled with a suitable molding material 74 such as RTV silicone. After the molding material 74 has set, the mold 70 may be opened and the male plug 22 and underwire 20 removed from the mold 70. It is desirable that the loop 21 of the underwire 20 be positioned in the mold 70 so that the male plug 22 completely encapsulates the loop 21 so that no portion of the loop 21 can contact the skin of the wearer. It has been discovered that RTV silicone such as the Silastic brand manufactured by Dow Corning provides the appropriate degree of strength and resilience suitable for the practice of the present invention although the present invention is not limited thereto. Once the underwire 20 with the molded-in male plug 22 is removed from the mold, the underwire 20 may be further shaped on a torso cast of the patient. As noted above, the torso cast may be modified with a depression in the area where the male plug 22 provides the spring bias against the chest wall of the patient. Further shaping of the underwire 20 may be performed on the patient directly for a custom fit.

In use the wearer simply dons the underwire bra in a normal fashion. The cup, which is adapted to receive the breast prosthesis is lowered, thereby exposing the retention fixture on the underwire bra. The breast prosthesis is fixed into position by "plugging" the retention fixture into the attachment fixture. The cup of the bra may then be positioned to cover the breast prosthesis and the strap assumed over the shoulder. Removing the breast prosthesis is simply the reverse of the steps described above.

The present invention has been described with reference to certain preferred and alternative embodiments which are intended to be exemplary only and not limiting to the full scope of the present invention as set forth in the appended claims.

What is claimed is:

1. In combination, a breast prosthesis and a bra adapted to be worn with the breast prosthesis by a mastectomy patient, comprising:

a breast prosthesis having first attachment means; and a bra having second attachment means, said first and second attachment means being adapted for releasible interconnection one to the other; and wherein said bra further comprises an underwire and further wherein said second attachment means is affixed to said underwire;

wherein said underwire further comprises a loop portion and further wherein said second attachment means is affixed to said loop portion.

2. The combination of claim 1 wherein said underwire further comprises spring means for biasing said second attachment means against the chest wall of the mastectomy patient.

3. The combination of claim 2 wherein said breast prosthesis comprises an anterior side and a posterior side and said first attachment means is molded into said posterior side of said breast prosthesis.

4. The combination of claim 3 wherein said first attachment means comprises a female plug and said second attachment means comprises a male plug for snapwise releasable interconnection to said female plug.

5. The combination of claim 4 wherein said male plug is molded around said loop portion of said underwire.

6. In combination, a breast prosthesis and a bra adapted to be worn with the breast prosthesis by a mastectomy patient, comprising:

a breast prosthesis having first attachment means; and a bra having second attachment means, said first and second attachment means being adapted for releasible interconnection one to the other; and wherein said bra further comprises spring means for biasing said second attachment means against the chest wall of the mastectomy patient.

7. The combination of claim 6 wherein said first attachment means comprises a female plug and said second attachment means comprises a male plug for snapwise releasible interconnection to said female plug.

8. In combination, a breast prosthesis and a bra adapted to be worn with the breast prosthesis by a mastectomy patient, comprising:

a breast prosthesis comprising an anterior side and a posterior side adapted to be presented toward the patient and having only one female plug molded into a central portion of said posterior side of said breast prosthesis; and a bra having only one male plug for snapwise releasible interconnection to said female plug.

9. The combination of claim 8 wherein said bra further comprises an underwire and further wherein said male plug is affixed to said underwire.

10. The combination of claim 9 wherein said underwire further comprises a loop portion and further wherein said male plug is affixed to said loop portion.

11. The combination of claim 10 wherein said underwire further comprises spring means for biasing said male plug against the chest wall of the mastectomy patient.

12. The combination of claim 11 wherein said male plug is molded around said loop portion of said underwire.

* * * * *